United States Patent [19]

Siegemund et al.

[11] Patent Number: 4,532,366
[45] Date of Patent: Jul. 30, 1985

[54] PERFLUORINATED VINYL ETHERS CONTAINING A SECONDARY HYDROGEN ATOM, POLYMERS FORMED THEREFROM AND A PROCESS FOR THE PREPARATION OF THE MONOMERS

[75] Inventors: Günter Siegemund, Hofheim am Taunus; Werner Schwertfeger, Langgöns, both of Fed. Rep. of Germany

[73] Assignee: Hoechst Aktiengesellschaft, Fed. Rep. of Germany

[21] Appl. No.: 467,178

[22] Filed: Feb. 16, 1983

[30] Foreign Application Priority Data

Feb. 27, 1982 [DE] Fed. Rep. of Germany ....... 3207143

[51] Int. Cl.³ .............................................. C07C 43/11
[52] U.S. Cl. ..................................... 568/615; 526/247; 568/674; 568/685; 568/616
[58] Field of Search ..................... 568/615, 685, 674; 526/247

[56] References Cited

U.S. PATENT DOCUMENTS 3,114,778 12/1963 Fritz et al. ........................ 568/685
3,450,684 6/1969 Darby .............................. 526/247
3,752,789 8/1973 Khan ............................... 526/247
3,896,179 7/1975 Resnick ............................ 568/685
4,418,186 11/1983 Yamabe et al. .................... 526/247

Primary Examiner—Harry Wong, Jr.
Attorney, Agent, or Firm—Connolly and Hutz

[57] ABSTRACT

New perfluorinated vinyl ethers containing a secondary hydrogen atom in the molecule of the formula I

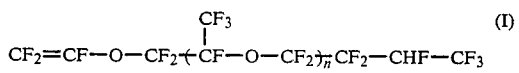

in which n is 0–5, preferably 0–3 and particularly 0–2, are useful intermediate products (particularly for the preparation of polymeric intermediates and of perfluorinated cation exchangers containing carboxyl groups) and are prepared by (a) reacting 3-H-perfluorobutyryl fluoride II

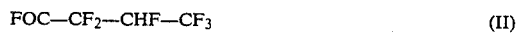

with hexafluoropropene epoxide III

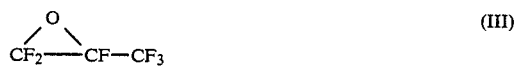

to give the acid fluoride IV

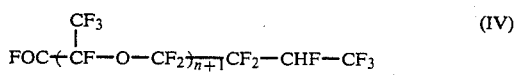

in which n has the same meaning as in formula I, (b) pyrolyzing the acid fluoride IV, as such or after conversion into the corresponding alkali metal carboxylate, at elevated temperature and (c) isolating the vinyl ether I formed in the pyrolysis.

9 Claims, No Drawings

PERFLUORINATED VINYL ETHERS CONTAINING A SECONDARY HYDROGEN ATOM, POLYMERS FORMED THEREFROM AND A PROCESS FOR THE PREPARATION OF THE MONOMERS

Perfluorinated vinyl ethers are compounds containing the —O—CF=CF$_2$ group attached to a perfluorinated organic radical. In most cases they are processed by homopolymerization or copolymerization (preferably with unsaturated monomers which are also perfluorinated) to give polymers having valuable technical properties in use.

Amongst the perfluorinated vinyl ethers which are processed further, for example, by the polymerization processes according to German Auslegeschrift No. 1,806,097 and German Offenlegungsschrift No. 2,639,109 there are, inter alia, also perfluorinated vinyl ethers which still contain a primary hydrogen atom; these perfluorinated vinyl ethers are:

$$CF_2=CF-O-(CF_2)_n-CF_2H \text{ and}$$

$$CF_2=CF-O-CF_2-\underset{\underset{CF_3}{|}}{CF}-O-(CF_2)_n-CF_2H$$
(n = 0–10)

If the perfluorinated vinyl ethers still contain an ester group in the molecule, polymers containing ester groups which can be saponified in a known manner are formed after the polymerization. The resulting fluorocarbon polymers containing carboxyl groups possess cation exchange properties and are, therefore, mainly used as cation exchange membranes in electrolytic cells, in particular in chloro-alkali electrolysis. An example of a route for the preparation of such perfluorinated cation exchangers is described, for instance, in the article by Maomi Seko "Ion-Exchange Membrane for the Chloro-Alkali Process" (submitted at the 159th meeting of the Electrochemical Society, Minneapolis, Minn. on 13th May 1981); this preparative route is shown below, as follows:

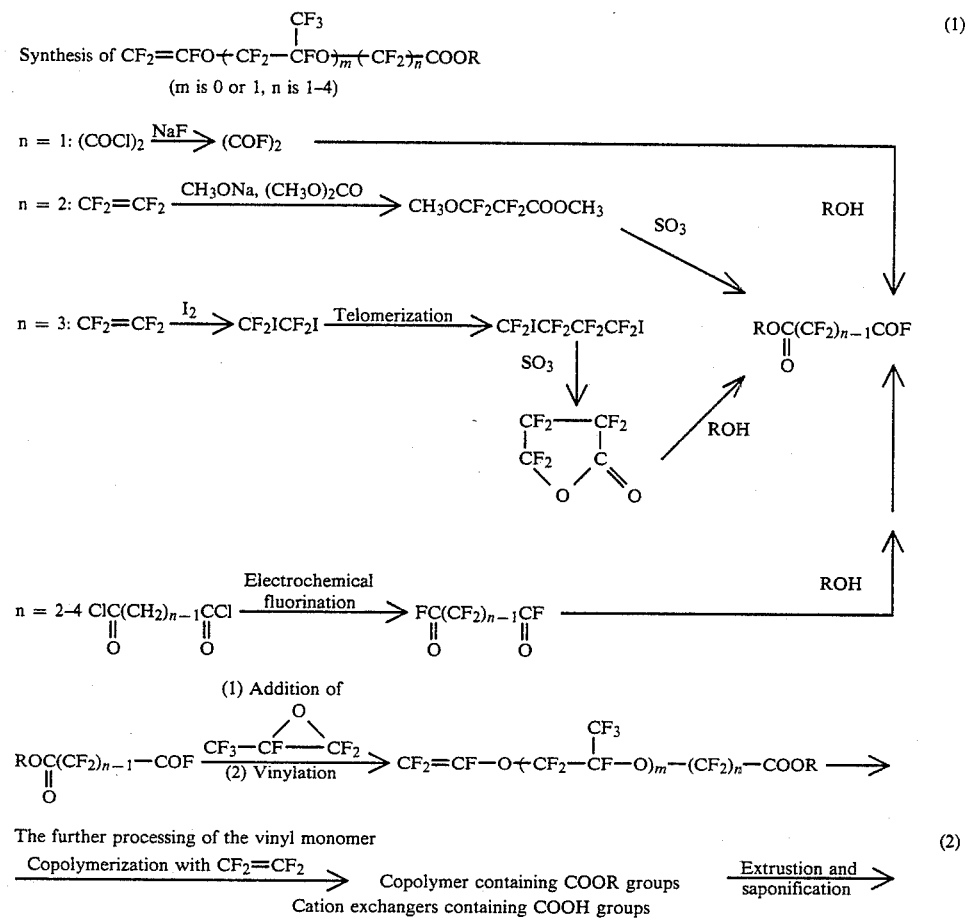

(1)

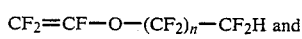

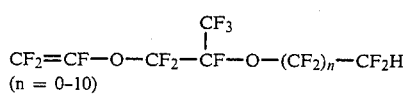

(2)

The typical route of synthesis for the preparation of perfluorinated cation exchangers containing carboxyl groups shows that the carboxylic acid group has to be introduced, in the form of the reactive ester group, at an early stage of the synthesis route—in any case considerably prior to the polymerization. Account must, therefore, be taken of the reactivity of this group in all the reaction stages following the introduction of the carboxylic ester group, and, if necessary, special measures must be taken to ensure its preservation.

It was, therefore, required to find a route in which the ester or carboxyl group is not introduced until the end of the entire synthesis of the appropriate perfluorinated cation exchangers.

This object can, admittedly, be achieved in principle via the known perfluorinated vinyl ethers containing a primary hydrogen atom in the molecule, but not to an extent sufficient to satisfy the considerable demand for more advantageous and cheaper processes for the preparation of perfluorinated cation exchangers.

A substantial further contribution towards achieving the intended object has, therefore, been made in accordance with the invention by providing a number of new perfluorinated vinyl ethers containing a secondary hydrogen atom; the new compounds possess the formula I below:

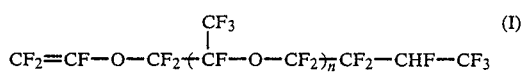

$$CF_2=CF-O-CF_2+CF-O-CF_2)_n CF_2-CHF-CF_3 \quad (I)$$
(with $CF_3$ branch on the first internal CF)

in which n is 0–5, preferably 0–3 and particularly 0–2.

The compounds can be homopolymerized and copolymerized (in the latter case with $CF_2=CF_2$, for example) by known processes—such as are, for example, described in the publications mentioned initially, German Auslegeschrift No. 1,806,097 and German Offenlegungsschrift No. 2,639,109. The polymers—which are also new—are then composed of macromolecules containing the side chain end groups —CHF—CF$_3$, which can be converted into functional groups and transformed into carboxyl groups by the process of U.S. patent application Ser. No. 467,179, filed Feb. 16, 1983, now U.S. Pat. No. 4,471,076 (Blickle et al), issued Sept. 11, 1984; this transformation is effected by reacting the polymers (containing the side chain end groups —CHF—CF$_3$) with peroxodisulfuryl difluoride FSO$_2$O—O—SO$_2$F to give the corresponding fluorosulfato derivatives containing the side chain end groups

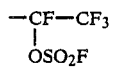

$$-CF-CF_3$$
$$|$$
$$OSO_2F$$

and decomposing the latter in the presence of catalytic amounts of alkali metal fluorides and/or aprotic nitrogen bases to give the corresponding ketones containing the side chain end groups.

$$-C-CF_3$$
$$\parallel$$
$$O$$

(in which the keto group can also be present in the form of a hydrate or semi-ketal in the presence of water or alcohols, respectively) and hydrolyzing the ketones to give the products containing the carboxyl group (preferably in a strongly basic medium):

$$-C-CF_3 \xrightarrow{H_2O} -C-OH + HCF_3$$
$$\parallel \qquad\qquad \parallel$$
$$O \qquad\qquad\quad O$$

The new compounds of the formula I and the polymers therefrom thus make possible a route of access to perfluorinated cation exchange polymers containing carboxyl groups which is advantageous and constitutes an advance. This route of access is advantageous and constitutes an advance in particular because—in contrast with the relevant state of the art—the carboxyl groups are not introduced until the end of the entire synthesis route.

The new compounds of the formula I are prepared in accordance with the invention by (a) reacting 3-H-perfluorobutyryl fluoride (II)

$$FOC-CF_2-CHF-CF_3 \quad (II)$$

with hexafluoropropene epoxide (III)

$$\begin{array}{c} O \\ / \backslash \\ CF_2\text{---}CF-CF_3 \end{array} \quad (III)$$

in the presence of at least one ionic fluoride as catalyst and an inert, aprotic-polar solvent, at temperatures between about −30° and about +100° C., preferably between about 0° and about +50° C., to give the acid fluoride of the formula IV

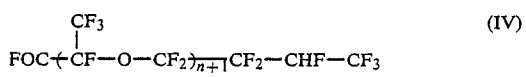

$$FOC+CF-O-CF_2)_{\overline{n+1}}CF_2-CHF-CF_3 \quad (IV)$$
(with $CF_3$ branch)

in which n has the same meaning as in formula I, (b) pyrolyzing the acid fluoride IV, as such or after conversion into the corresponding alkali metal carboxylate, at temperatures between about 100° and about 600° C., and (c) isolating the vinyl ether of the formula I formed in the pyrolysis.

Stages (a) and (b) of the process can be represented (diagrammatically) in terms of formulae as follows:

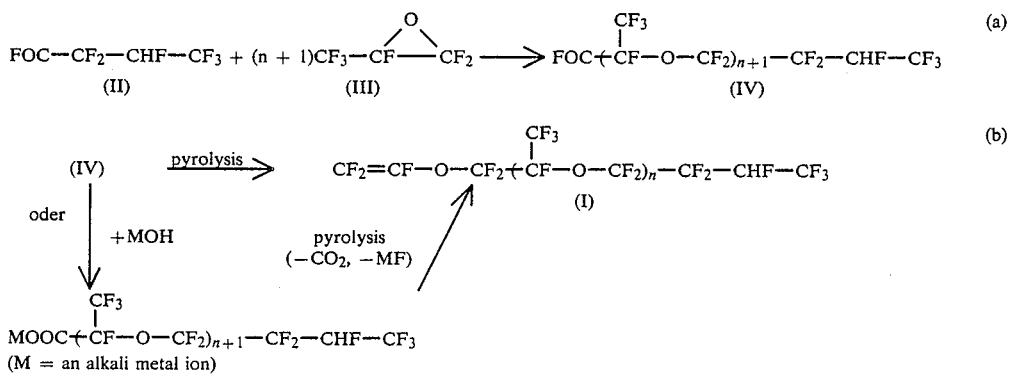

The starting compound for the process - 3-H-perfluorobutyryl fluoride (II) - is a known compound which is accessible, for instance, by the following route of synthesis [J. Amer. Chem. Soc. 77 (1955), pages 910 et seq. and converting the acid chloride CLOC—CF$_2$—CHF—CF$_3$ into the acid fluoride in a known manner]:

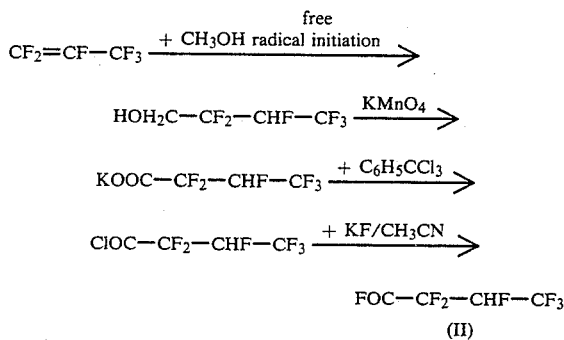

The individual stages of the process according to the invention for the preparation of the compounds I can, in principle, be carried out by the methods customary for such reactions, such as are described, for example, in U.S. Pat. No. 3,114,778 for the process of that patent for the preparation of perfluorovinyl ethers from perfluoroalkanoic acid fluorides and hexafluoropropene epoxide and also pyrolysis of the reaction products formed, as such or in the form of the corresponding alkali metal carboxylates.

Accordingly, any possible ionic fluorides can be employed, in principle, as catalysts in stage (a) of the process according to the invention; however, it is preferable to employ the alkali metal fluorides, quaternary ammonium fluorides and silver fluoride, particularly the alkali metal fluorides (and within these, in turn, mainly potassium fluoride and cesium fluoride). The individual catalyst compounds can be used either on their own or as a mixture.

The amount of catalyst ranges, in general, between about 0.01 and about 5, preferably between about 0.01 and about 1, % by weight, relative to the total amount of hexafluoropropene epoxide employed.

Preferred inert, aprotic-polar solvents are nitriles (acetonitrile, benzonitrile and the like), ethers (in particular polyalkyl ethers, such as ethylene glycol dimethyl ether, diethylene glycol dimethyl ether, tetraethylene glycol dimethyl ether and the like) and others; it is also possible to use solvents such as dimethyl sulfoxide, N-methylpyrrolidone and the like.

The reaction temperature can vary within relatively wide limits; it is preferably between about −30° and about 100° C., in particular between about 0° and about 50° C. Either normal pressure or an excess pressure or a vacuum is possible for the reaction pressure; a slight excess pressure or normal pressure is preferred.

A preferred mode of carrying out reaction stage (a) comprises initially taking 3-H-perfluorobutyryl fluoride II, the catalyst and an inert, aprotic-polar solvent in a reaction vessel, and introducing hexafluoropropene epoxide III while stirring. When the reaction is complete, the mixture is worked up by distillation. Method for carrying out reaction stage (b):

If the acid fluoride IV obtained in stage (a) is pyrolyzed direct as such, a temperature of about 300° to 600° C. is employed. The temperature can also be somewhat lower in the presence of catalysts, such as, for instance, sodium sulfate.

It is also possible to employ a lower temperature if the acid fluoride IV is first converted into the corresponding alkali metal carboxylate (for example by means of KOH). In general, the alkali metal carboxylate is pyrolyzed at about 170° to 250° C., or at an even lower temperature (down to about 100° C.) in the presence of an inert diluent, such as, for example, paraffin oil.

The preferred reaction pressure for the pyrolysis is normal pressure or a vacuum.

A preferred embodiment of reaction stage (b) comprises saponifying the acid fluoride IV by dropwise addition of aqueous alkali, drying the resulting alkali metal salt and pyrolyzing it at an elevated temperature in vacuo.

The vinyl ether I formed in the pyrolysis is then advantageously isolated and purified in reaction stage (c) by fractional distillation.

The yields of the process are normally between about 60 and 70% of theory.

The invention will now be illustrated in greater detail by the following example.

EXAMPLE (a) Reacting 3-H-perfluorobutyryl fluoride with hexafluoropropene epoxide

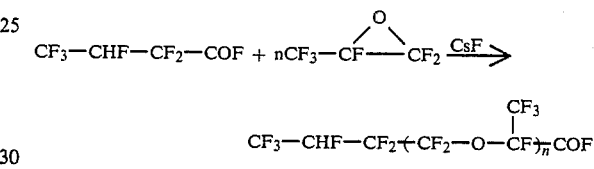

30 g (0.2 mole) of CsF, 100 ml of tetraglyme and 740 g (3.73 moles) of $CF_3$—$CHF$—$CF_2$—$COF$ are initially put into a glass autoclave, equipped with a paddle stirrer and a cooling jacket. Hexafluoropropene epoxide (HFPO) is injected while stirring vigorously. The gas is absorbed immediately with an exothermic reaction. The internal temperature is kept at about 30° C. by cooling. Altogether, 1,050 g (6.3 moles) of HFPO are passed in as gas. This requires 1.5 hours. The mixture is stirred at room temperature for approx. one hour more and is then distilled through a packed column. This gives the following compounds:

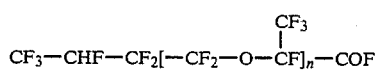

n=1: boiling point 90°–93° C./755 mm Hg; 655 g=48% of theory.

n=2: boiling point 82°–84° C./100 mm Hg; 455 g=23% of theory.

A further batch containing 751 g (3.8 moles) of $CF_3$—$CHF$—$CF_2$—$COF$, 20 g (0.13 mole) of CsF, 100 ml of tetraglyme and 1,909 g (11.5 moles) of HFPO (the HFPO is passed in as gas under normal pressure) gives the following fractions:

n=1: 404 g=29%
n=2: 774 g=38%
n=3: 307 g=12%, boiling point 85°–88° C./21 mm Hg
(b₁) 3-H-Perfluoro-n-butyl-vinyl ether

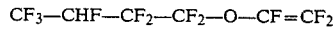

399 g (1.1 moles) of 6-H-3-oxaperfluoro-2-methylheptanoyl fluoride - i.e. the compound prepared in stage (a)

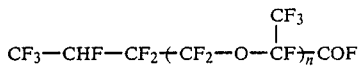

in which n=1—are reacted with aqueous caustic soda solution at 20°–40° C. until the addition of phenolphthalein shows a slight red coloration lasting for 30 minutes. After evaporating the solution, the resulting salt is dried in vacuo at approx. 110° C. The salt is pulverized and suspended in one liter of paraffin oil, which is heated at approx. 200° to 250° C. The vinyl ether is formed with liberation of $CO_2$; the bulk of it distils off.

(c₁) A small quantity of the vinyl ether also condenses in the cold trap downstream (−78° C.). Distillation gives 205 g (63%) of the pure vinyl ether of boiling point 76°–78° C./760 mm Hg.

$^1$H-NMR: =5.05 (dm, CHF, J=44 Hz).

$^{19}$F-NMR: = −74.8 (m, 3F, $CF_3$), −86.8 (dm, 1F, —CHF—$CF_2$—, $^2J$=140 Hz), −89.3 (dm, 1F, —CHF—$CF_2$—, 2J=140 Hz), −114.3 (dd, 1F, —O—CF=$CF_2$ trans, J=87 and 65 Hz), —122.4 (ddm, 1F, —O—CF=$CF_2$, J=110 and 87 Hz), −124.2 (dm, 1F, —$CF_2$—O—, $^2J$=285 Hz), −131.7 (dm, 1F, —$CF_2$—O—, $^2J$=285 Hz), −135.9 (ddm, 1F, —O—CF=$CF_2$ cis, J=110 and 65 Hz), −213.5 (m, 1F, CHF).

(b₂) 2-(3-H-Perfluoro-n-butoxy)-perfluoropropyl-vinyl ether

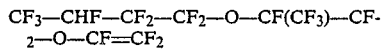

765 g (1.44 moles) of 9-H-3,6-dioxaperfluoro-2,5-dimethyldecanoyl fluoride - i.e. the compound

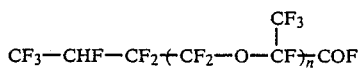

having n=2 prepared in stage (a)—are converted into the sodium salt as described in paragraph b₁. The dry salt is pyrolyzed under a pressure of 5 mm Hg and at an oil bath temperature of approx. 230° C.

(c₂) The crude pyrolysate is purified by distillation through a good column. 423 g (63%) of the vinyl ether are obtained at a boiling point of 57°–58° C./50 mm Hg.

$^1$H-NMR: =5.00 (dm, CHF, J=44 Hz).

$^{15}$F-NMR: = −75.8 (m, 3F, $CF_3$), −80.5 (m, 3F, $CF_3$),

−83.3 (m, 2F, $CF_2$—O), −85.2 (m, 2F, $CF_2$—O),

−113.9 (dd, 1F, —O—CF=$CF_2$ trans), −122.2 (ddm, 1F,

—O—CF=$CF_2$), −123.8 (dm, 1F,

—CHF—$CF_2$, $^2J$=285 Hz), −131.4 (ddm, 1F, —CHF—$CF_2$—, $^2J$=285 Hz), −136.1 (ddm, 1F, —O—CF=$CF_2$ cis), −145.4 (m, 1F, CF), −213.6 (m, 1F, CHF).

We claim

1. A perfluorinated vinyl ether containing a secondary hydrogen atom of the formula I

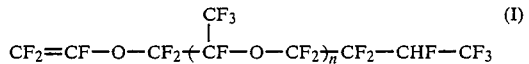

in which n is 0–5.

2. A perfluorinated vinyl ether according to claim 1, wherein n is 0–3.

3. A perfluorinated vinyl ether according to claim 2, wherein n is 0–2.

4. A process for the preparation of the perfluorinated vinyl ether containing a secondary hydrogen atom of the formula I of claim 1 by (a) reacting 3-H-perfluorobutyryl fluoride II $$FOC—CF_2—CHF—CF_3 \quad (II)$$

with hexafluoropropene epoxide (III)

in the presence of at least one ionic fluoride as catalyst and of an inert, aprotic-polar solvent, at temperatures between about −30° and about +100° C., to give the acid fluoride of the formula IV

in which n is 0–5, (b) pyrolyzing the acid fluoride IV, as such or after conversion into the corresponding alkali metal carboxylate, at temperatures between about 100° and about 600° C., and (c) isolating the vinyl ether of the formula I formed in the pyrolysis.

5. A process according to claim 4, wherein n is 0–3.

6. A process according to claim 4, wherein n is 0–2.

7. A process according to claim 4, wherein said temperatures of said step (a) are between about 0° and about 50° C.

8. A process according to claim 7, wherein n is 0–3.

9. A process according to claim 7, wherein n is 0–2.

* * * * *